(12) United States Patent
Li et al.

(10) Patent No.: US 9,226,993 B2
(45) Date of Patent: Jan. 5, 2016

(54) BIOMATERIAL SCAFFOLDS WITH KERATIN FOR TISSUE ENGINEERING

(75) Inventors: Yi Li, Kowloon (CN); Jiashen Li, Kowloong (CN); Junyan Hu, Kowloon (CN); Lin Li, Kowloon (CN)

(73) Assignee: The Hong Kong Polytechnic University, Hung Hom, Kowloon, Hong Kong (CN)

( * ) Notice: Subject to any disclaimer, the term of this patent is extended or adjusted under 35 U.S.C. 154(b) by 2155 days.

(21) Appl. No.: 12/216,718

(22) Filed: Jul. 10, 2008

(65) Prior Publication Data

US 2010/0008969 A1   Jan. 14, 2010

(51) Int. Cl.
| | | |
|---|---|---|
| *A61F 2/00* | (2006.01) | |
| *A61L 27/22* | (2006.01) | |
| *A61L 27/18* | (2006.01) | |
| *A61L 27/56* | (2006.01) | |

(52) U.S. Cl.
CPC .............. *A61L 27/227* (2013.01); *A61L 27/18* (2013.01); *A61L 27/56* (2013.01)

(58) Field of Classification Search
USPC .................................................. 424/426, 428
See application file for complete search history.

(56) References Cited

U.S. PATENT DOCUMENTS

| | | | |
|---|---|---|---|
| 6,124,265 A | 9/2000 | Timmons et al. | |
| 6,159,495 A | 12/2000 | Timmons et al. | |
| 6,432,435 B1 * | 8/2002 | Timmons et al. | 424/422 |
| 2003/0114936 A1 * | 6/2003 | Sherwood et al. | 623/23.58 |

* cited by examiner

*Primary Examiner* — Dennis J Parad
(74) *Attorney, Agent, or Firm* — Wilkinson $ Grist; George G. Wang

(57) ABSTRACT

The present invention relates to methods for preparing porous natural or synthetic material scaffolds with keratin for improving cell affinity.

10 Claims, 3 Drawing Sheets

BIOMATERIAL SCAFFOLDS WITH KERATIN FOR TISSUE ENGINEERING

BACKGROUND

An enormous expenditure of health-care resources was required for the repair and replacement of diseased tissue structures and organs. The most common treatment, replacement with an autograft, produces less than optimal results. However, the supply of autograft, and even allograft, is very limited. Engineering tissues and organs with mammalian cells and a scaffolding material as emerged as a promising alternative approach in the treatment of malfunctioning or lost organs compared to the use of harvested tissues and organs (see Langer, R. S. and J. P. Vacanti, "Tissue engineering: the challenges ahead," Scientific American 280(4), 86 (1999)). In this approach, a temporary scaffold is needed to serve as an adhesive substrate for the implanted cells and a physical support to guide the formation of the new organs. Accordingly, the scaffold materials must be custom-engineered to match the biomechanical, biochemical, and biological needs of the specific tissue or organ they are designed to replace. Transplanted cells adhere to the scaffold, proliferate, secrete their own extracellular matrices (ECM) and stimulate new tissue formation (see Langer, R. and J. Vacanti, "Tissue Engineering", Science 260 (5110), 920-926 (1993); Hubbell, J. A., "Biomaterials in Tissue Engineering", Bio/Technology 13, 565 (1995); and Saltzman, W. M., "Cell interactions with polymers," Principles of Tissue Engineering, R. Lanza, R. Langer, and W. Chick, Editors (1997) Academic Press, R. G. Landes Company, Austin, Tex., 225). During this process, the scaffold must be degraded and eliminated gradually and disappears eventually. Therefore, in addition to facilitating cell adhesion, promoting cell growth, and allowing the retention of differentiated cell functions, the scaffold should be biocompatible, biodegradable, highly porous with a large surface/volume ratio, mechanically strong, and malleable into desired shapes. The biophysical and biomechanical properties of a biomaterial scaffold are crucial for the outcome of tissue engineering. In many circumstances, the material selection is a compromise among the many physical and biological requirements. Synthetic biodegradable polymers have been attractive candidates for scaffolding materials because they degrade as the new tissues are formed, eventually leaving nothing foreign to the body. And their physical and biological properties can be controlled and tailored through different synthetic conditions and methods.

Aliphatic polyesters are one class that consists of synthetic biodegradable polymers, such as poly(glycolic acid) (PGA), poly(lactic acid) (PLA), and their copolymer of poly-(DL-lactic-co-glycolic acid)(PLGA). PLA, PGA, and PLGA have been approved by the U.S. Food and Drug Administration for some human clinical applications, such as surgical sutures and implantable devices. One of their potential advantages is that their degradation rate can be adjusted to match the rate of regeneration of the new tissue. With sufficient mechanical strength, they can keep this framework until the new tissue forms. They also can be fabricated to be the same complicated shapes or structures as the tissues or organs to be replaced.

Although such synthetic materials are widely used, they still have some disadvantages, such as hydrophobicity, the lack of cell-recognition signals, etc. These results show that there is no sufficient cell adhesion on the surface of these polymer materials. Their interactions with the host environment still have much potential for improvement. How to improve the biomaterial/cell interaction for eliciting the controlled cellular adhesion and maintaining differentiated phenotypic expression has become one of the major challenges in the field of tissue engineering.

To overcome the drawbacks associated with synthetic biodegradable polymer materials, much attention has focused on coating cell adhesion-enhancing agents on these materials, such as collagen, bone-like apatite, hydroxyapatite, on the surface of polymer materials.

It is an object of the present invention to overcome the disadvantages and problems in the prior art.

DESCRIPTION

The present invention relates to methods for preparing porous natural or synthetic material scaffolds with keratin for improving cell affinity.

These and other features, aspects, and advantages of the apparatus and methods of the present invention will become better understood from the following description, appended claims, and accompanying drawings where:

The following description of certain exemplary embodiment(s) is merely exemplary in nature and is in no way intended to limit the invention, its application, or uses.

Figure 1:
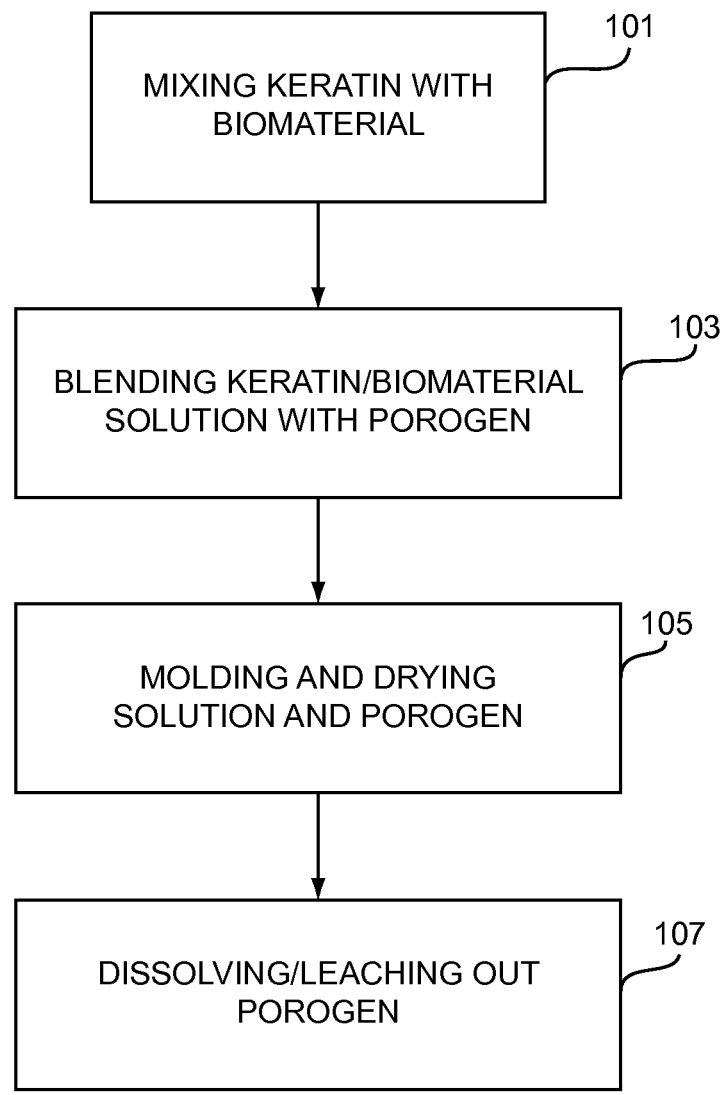
FIG. 1 shows an embodiment of the method of the present invention.
Figure 2:
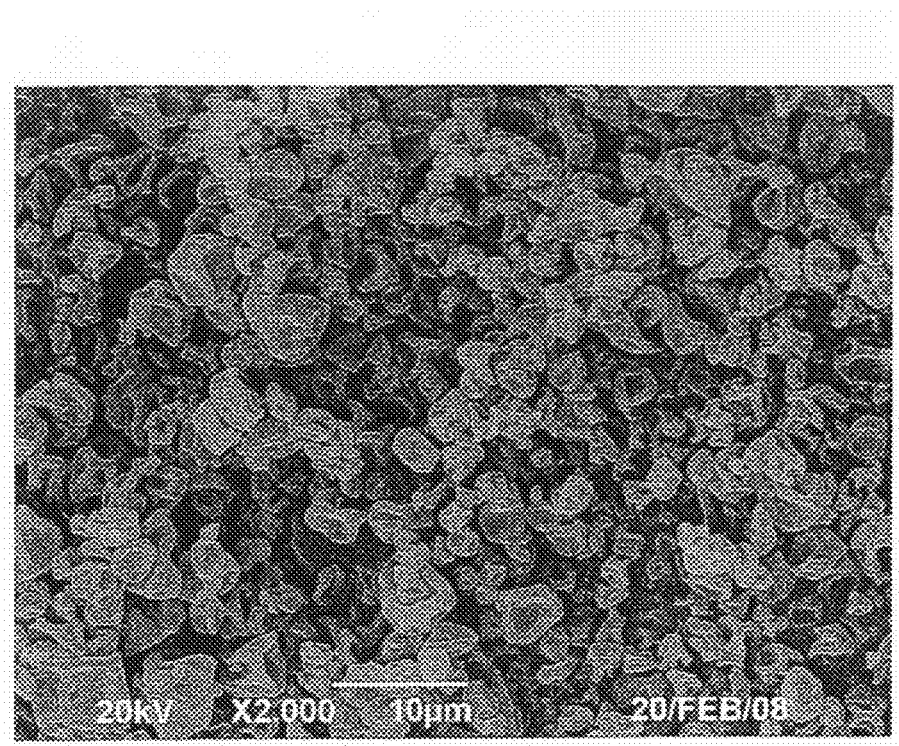
FIG. 2 is a SEM of wool keratin particles.
Figure 3:
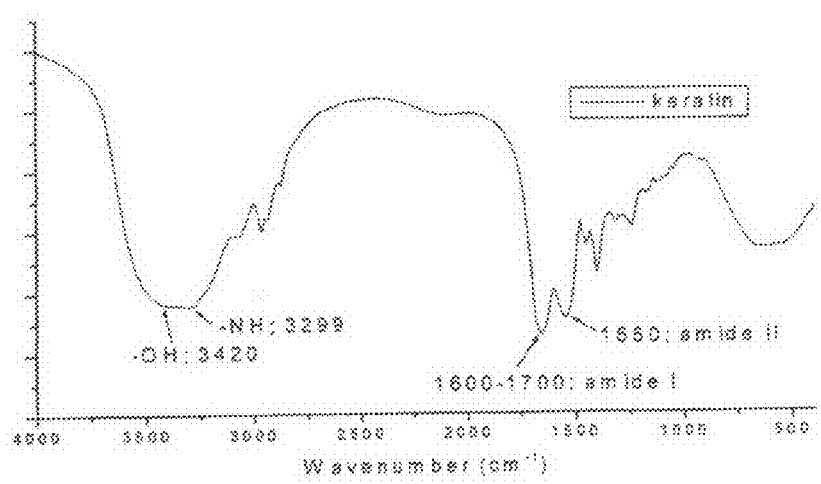
FIG. 3 is an FTIR spectra of wool keratin.
Figure 4:
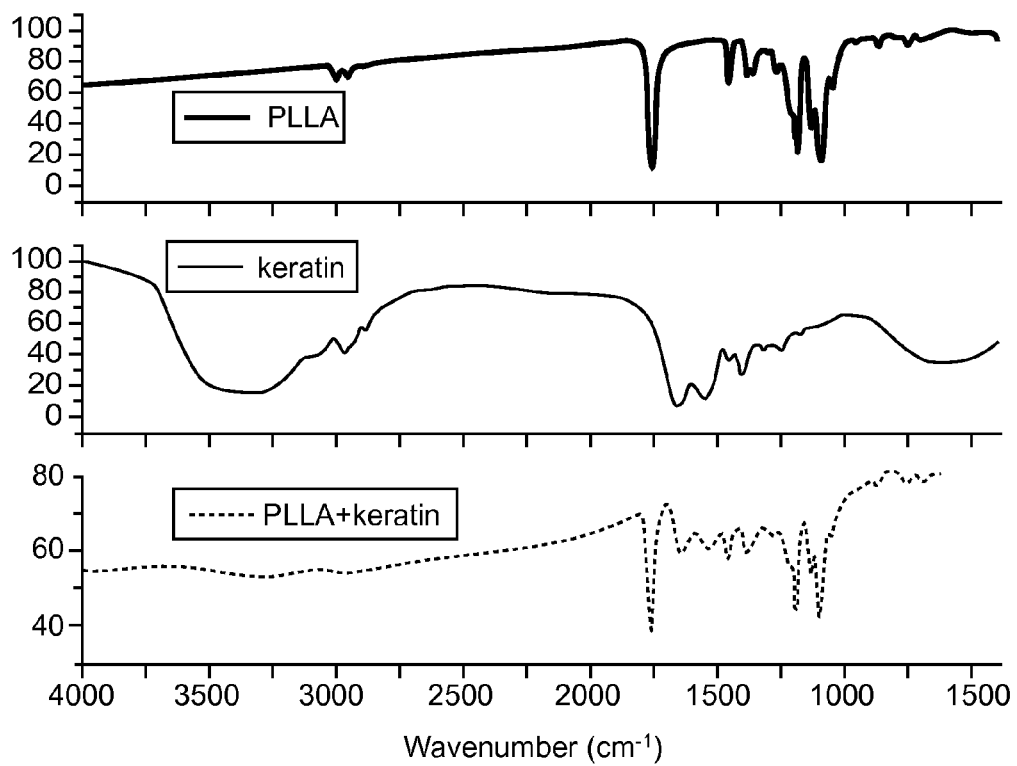
FIG. 4 is an FTIR spectra of pure PLLA.

Now, to FIGS. 1-5,

FIG. 1 is an embodiment of the method of the present invention. As a first step, keratin is mixed with a biomaterial 101. Keratins are the major structural fibrous proteins constructing hair, wool, nail, and so on, which are characteristically abundant in cysteine residues (7-20% of the total amino acid residues). As alternative natural proteinous biomaterials for collagen, wool keratins have been demonstrated to be useful for fibroblasts and osteoblasts, owing to their cell adhesion sequences, arginine-glycine-aspartic acid (RGD) and leucine-aspartic acid-valine (LDV), biocompatibility for modification targets. Moreover, they are biodegradable in vitro (by trypsin) and in-vitro (by subcutaneous embedding in mice). FIG. 1 is an embodiment of a scanning electron microscope image of wool keratin particles.

The biomaterial can be natural or synthetic, and is selected from the group consisting of poly(lactide-co-glycolide) (PLGA), poly(lactide)(PLLA), polyglycolic acid (PGA), polyanhydrides, poly(ortho ethers), poly caprolactone, polyethylene glycol (PEG), polyurethane, copolymers thereof, and mixtures thereof.

The keratin-biomaterial solution is then mixed with porogen 103. Porogen is selected from the group consisting of sodium chloride, sodium sulfate, potassium chloride, sodium iodide, sodium fluoride, potassium fluoride, sodium nitrate, sodium iodate, mixtures thereof, sodium hydroxide, fructose, saccharin, glucose, mixtures thereof, paraffin, beeswax, mixtures thereof, naphthalene, and gelatins. The porogen may be formed into any shape as desired and/or necessary. In a preferred embodiment, the predetermined shape is selected from the group consisting of cubic or other geometrically shaped crystals, spheres, fibers, discs, regular geometric shapes, irregular geometric shapes, and mixtures thereof.

The solution and porogen are then dried 105, and then the porogen is dissolved or leached out from the solution 107.

It is to be understood that the cell adhesion-enhancing keratin used in the present invention may include a liquid. Preferably, the cell adhesion-enhancing keratin when mixed is at least one of a solution, a suspension, a melt, a slurry, flowable powders, flowable fibers, flowable pastes, and mixtures thereof. It is to be understood that the natural or synthetic biomaterials may be any composition which flows adequately for blending purposes. In one preferred embodiment, the liquid is a solvent and the biomaterial, natural or synthetic, is a polymeric composition.

The method of the present invention may be performed continuously, i.e., it may be automated wherein the porogen is used to print the 3-D structure, or in batches, manually or automatically.

EXAMPLES

Example 1

Poly(L-lactic acid) PLLA with an inherent viscosity of 7.0 dl/g was purchased from PURAC (Netherlands) and was used as received. Poly(vinyl alcohol)(PVA) (88% hydrolyzed, average molecular weight 25,000 g/mol), paraffin (melting point 53-57° C.), 1,4-dioxane, and cyclohexane were purchased from Acros (Belgium). The nano wool keratin powders used in this study was acquired from Nano Sports Technologies Ltd. (Hong Kong).

Preparation of Paraffin Micro-Spheres

Paraffin micro-spheres were prepared by solidifying tiny paraffin drops in hot PVA solution. Briefly, a 1000 ml beaker with 500 ml water was heated to 60-70° C. PVA (2.5 g) was added into the water and stirred to make a 0.5% (g/ml) solution. 20 g paraffin was heated to melt in a glass vial and added into the PVA solution with stirring. The mixture was then poured into a container with 2000 ml cold water to solidify the small paraffin drops to form paraffin micro-spheres. Standard sieves were used to separate the paraffin micro-spheres into different size ranges (diameter from 100 to 500 µm). The paraffin micro-spheres were washed with distilled water for five times and dried in air.

Preparation of PLLA/Keratin Scaffolds

PLLA and keratin powder was dissolved in 1,4-dioxane with a desired concentration and ratios. The PLLA/keratin solution was then mixed with paraffin micro-spheres. A plastic syringe tube without end was used as the mold for preparing PLLA/keratin scaffold. Some of PLLA/keratin/paraffin micro-spheres suspension was poured into the mold. Caution was taken to ensure that there was no air bubble trapped inside the mold. The solution and paraffin spheres were compressed until no extra PLLA/keratin solution were found out of the mold. At this point, the paraffin spheres contacted each other and the inter space among paraffin spheres was fully filled with PLLA/keratin solution. The PLLA/keratin/paraffin micro-spheres scaffold was about 3 mm in thickness. After the scaffolds were dried in an incubator at 37° C. for 12 h, they were cooled down to the room temperature. Five scaffold samples were prepared for each PLLA/keratin ratio for each characterization.

The discs were immersed in 40 mL of cyclohexane at room temperature for 12 h to dissolve and remove the paraffin. The cyclohexane was changed every 3 h. After the discs with cyclohexane were frozen in a freezer (−20° C.) for more than 6 h, they were freeze-dried at 10° C. for 2 days and subsequently dried at room temperature under vacuum for 1 week to remove any remaining solvents.

Results and Discussion

Figure 5:
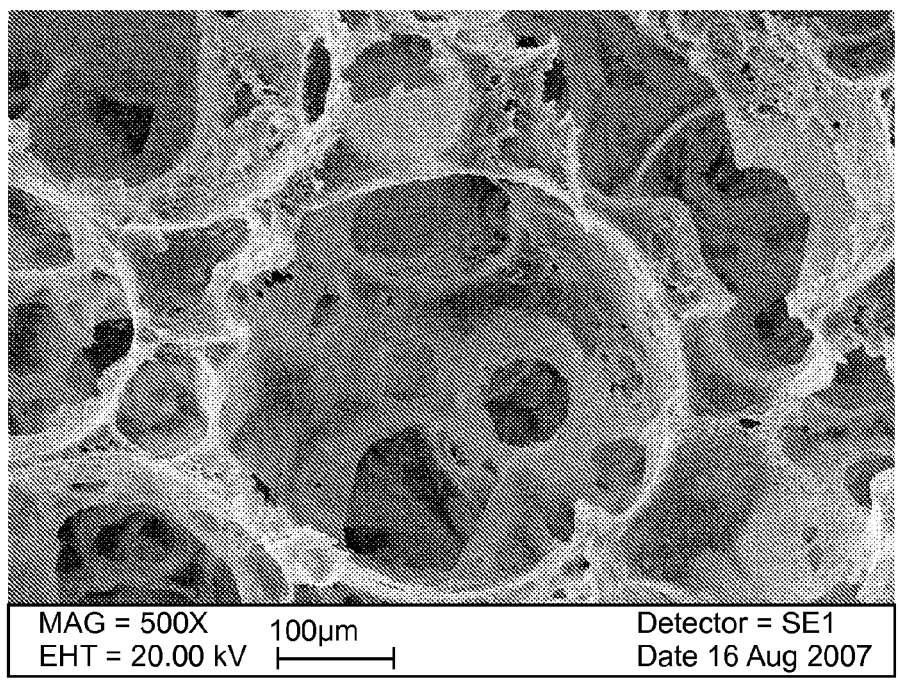
FIG. 5 is an SEM micrograph of PLLA/wool keratin scaffold.

Scanning electron microscopy (SEM) was used to examine the morphology. The PLLA/keratin scaffold was highly porous. The pores were well interconnected and reflected a negative replica of the paraffin microspheres (FIG. 5). After the paraffin micro-spheres were dissolved and removed, the space occupied by paraffin micro-spheres was emptied as pores which correspond in dimension to that of the paraffin micro-spheres used. The PLLA/keratin among the paraffin micro-spheres became the pore wall of the scaffold. The contact areas between two adjacent paraffin microspheres became small holes connecting the adjacent bigger pores. They contributed to the interconnectivity of the scaffold. The diameter of these holes was about 100 µm, which would adequately serve as the channels for cells, nutrients and waste to pass in and out of the scaffold. The pore size of the scaffold could be adjusted by choosing paraffin microspheres with different diameters (from 100 to 500 µm).

FTIR spectroscopy was used to gain additional information on the functional groups present of the PLLA/keratin. In the FTIR spectroscopy of pure keratin (FIG. 3), strong absorptions from 3250 to 3300 $cm^{-1}$ were N—H stretch which was in resonance with amide II overtone. Absorptions from 1600 to 1700 $cm^{-1}$ were mainly C=O stretching. The peak at 1550 $cm^{-1}$ was due to the N—H bending coupled with C—N stretching. The FTIR spectrum of PLLA/keratin (FIG. 4) showed two strong absorptions at 1600-1700 $cm^{-1}$ and 1550 $cm^{-1}$, which belonged to keratin. These analyses demonstrated that keratins were joined on PLLA scaffold.

Example 2

Cell Seeding

MC3TS osteoblast cells were cultured at 37° C. in a humidified atmosphere of 5% $CO_2$ in air, in flasks containing 6 ml Dulbecco's modified Eagle's medium (DMEM; Gibco), 10.0% fetal bovine serum (FBS; Gibco) and 1% penicillin/streptomycin. The medium was changed every third day. After 7-day culture, the MC3TS cells were removed from the flask, using trypsin, centrifuged and resuspended in DMEM medium to adjust cell density to $4 \times 10^6$ cells/mL. 25 µL (about $1 \times 10^5$ cells) of the cell suspensions were seeded evenly into the PLLA/wool keratin scaffolds with a micropipette. The seeded scaffolds were maintained in incubator for 2 h and culture medium was added to the wells. The medium was changed every 2 days. After incubation, any non-adherent cells on the samples were removed by aspirating the medium and washing with PBS solution.

MTT Assay

The MTT assay was used as a measure of relative cell viability. After the MC3T3 cells were cultured in scaffolds for 8 days, the cell viability was evaluated using the MTT assay (Acros, Belgium), in which 20 µL of MTT [3-(4,5-dimethylthiazol-2-yl)-2,5-diphenyltetrasodium bromide] (5 mg/L) was added to each well and incubated at 37° C. for 4 h. The blue formazan reaction product was then dissolved by adding 150 µL DMSO. The absorbance was analyzed using a microplate reader.

Alkaline Phosphatase Assay

Alkaline phosphatase (ALP) activity was measured using an alkaline phosphatase assay kit (Zhongsheng Beikong, China). Cells were incubated in scaffolds in a 96-well plate for 8 days. After removing the culture medium, the cell layers were washed with PBS and resuspended by vortexing them in 0.025 mL of deionized water with 0.1% Triton X-100. The cell pellets were disrupted via a cyclic freezing/thawing process. The prepared cell lysates were used to determine ALP activity according to the manufacturer's instructions.

Results and Discussion

MTT assay involves a reduction reaction which reduces MTT reagent to a flue formazan product when incubated with viable cells. Thus the absorbance of fromazan indirectly reflected the level of cell metabolism and this process is taken as a measure of the viability of cells in culture. Compared to the control, higher absorbance was obtained on PLLA/wool keratin scaffolds. Alkaline phosphatase activity was measured to assess the differentiated osteogenic activity of the cell constructs. The ALP activity of MC3T3 cultured on PLLA/wool keratin scaffolds were significantly higher than that on PLLA scaffolds control.

Having described embodiments of the present system with reference to the accompanying drawings, it is to be understood that the present system is not limited to the precise embodiments, and that various changes and modifications may be effected therein by one having ordinary skill in the art without departing from the scope or spirit as defined in the appended claims.

In interpreting the appended claims, it should be understood that:

a) the word "comprising" does not exclude the presence of other elements or acts than those listed in the given claim;

b) the word "a" or "an" preceding an element does not exclude the presence of a plurality of such elements;

c) any reference signs in the claims do not limit their scope;

d) any of the disclosed devices or portions thereof may be combined together or separated into further portions unless specifically stated otherwise; and e) no specific sequence of acts or steps is intended to be required unless specifically indicated.

The invention claimed is:

1. A method for combining a cell adhesion-enhancing keratin with a biomaterial scaffold, comprising the steps of:
   (a) mixing keratin with a biomaterial to form a keratin-biomaterial solution;
   (b) mixing porogen with said keratin-biomaterial solution to form a body;
   (c) drying said body; and
   (d) dissolving and leaching out the porogen from said body.

2. The method of claim 1, wherein said method is a continuous process.

3. The method of claim 1, wherein said method is a batch process.

4. The method of claim 1, wherein said keratin includes a liquid.

5. The method of claim 4, wherein said keratin is at least one of a solution, a suspension, a slurry, flowable powder, flowable fiber, flowable paste, and mixtures thereof.

6. The method of claim 1, wherein said porogen is selected from the group consisting of sodium chloride, sodium sulfate, potassium chloride, sodium iodide, sodium fluoride, potassium fluoride, sodium nitrate, sodium iodate, sodium hydroxide, fructose, saccharin, glucose, paraffin, beeswax, naphthalene, and gelatin.

7. The method of claim 6, wherein said porogen after being mixed with said keratin-biomaterial solution is formed into a shape of a cubic, geometrically-shaped crystals, geometric shapes, or mixtures thereof.

8. The method of claim 1, wherein said biomaterial is selected from group consisting of poly(lactide-co-glycolide) (PLGA), poly(lactide) (PLLA), polyglycolic acid (PGA), polyanhydrides, poly(ortho ethers), poly caprolactone, polyethylene glycol (PEG), polyurethane, copolymers thereof, and mixtures thereof.

9. The method of claim 1, wherein said keratin is fibrous or powdered.

10. The method of claim 1, further comprising the step, after mixing keratin with biomaterial solution, adding functional or inert additives to the solution.

\* \* \* \* \*